(12) United States Patent
Wang

(10) Patent No.: US 7,794,402 B2
(45) Date of Patent: Sep. 14, 2010

(54) ECHOGENIC NEEDLE CATHETER CONFIGURED TO PRODUCE AN IMPROVED ULTRASOUND IMAGE

(75) Inventor: Edwin Y. Wang, Tustin, CA (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 98 days.

(21) Appl. No.: 11/435,216

(22) Filed: May 15, 2006

(65) Prior Publication Data

US 2007/0265516 A1 Nov. 15, 2007

(51) Int. Cl.
*A61B 8/14* (2006.01)
(52) U.S. Cl. .................. 600/459; 600/372
(58) Field of Classification Search .......... 600/459, 600/462, 461, 463, 464, 466, 467, 479, 372–375, 600/385, 395
See application file for complete search history.

(56) References Cited

U.S. PATENT DOCUMENTS

| | | | |
|---|---|---|---|
| 3,984,911 A | 10/1976 | Krug et al. | |
| 4,052,989 A * | 10/1977 | Kline | 604/170.01 |
| 4,175,266 A | 11/1979 | Nakano et al. | |
| 4,234,887 A | 11/1980 | Vanderslice, Jr. | |
| 4,465,072 A * | 8/1984 | Taheri | 606/159 |
| 4,509,523 A | 4/1985 | Persner | |
| 4,960,134 A * | 10/1990 | Webster, Jr. | 607/116 |
| 5,045,072 A * | 9/1991 | Castillo et al. | 604/529 |
| 5,237,996 A * | 8/1993 | Waldman et al. | 600/374 |
| 5,242,429 A * | 9/1993 | Nwaneri et al. | 604/270 |
| 5,275,162 A | 1/1994 | Edwards et al. | |
| 5,286,413 A | 2/1994 | Hannecart et al. | |
| 5,322,520 A | 6/1994 | Milder | |
| 5,411,527 A | 5/1995 | Alt | |
| 5,431,168 A * | 7/1995 | Webster, Jr. | 600/435 |
| 5,471,988 A | 12/1995 | Fujio et al. | |
| 5,491,198 A * | 2/1996 | Shalaby et al. | 525/340 |
| 5,531,713 A * | 7/1996 | Mastronardi et al. | 604/263 |
| 5,558,517 A | 9/1996 | Shalaby et al. | |
| 5,591,142 A | 1/1997 | Van Erp | |
| 5,603,327 A * | 2/1997 | Eberle et al. | 600/467 |
| 5,772,590 A * | 6/1998 | Webster, Jr. | 600/374 |

(Continued)

FOREIGN PATENT DOCUMENTS

DE 2822829 A1 11/1979

(Continued)

OTHER PUBLICATIONS

Surface phosphonylation of low-density polyethylene; Allan et al.; Journal of Applied Polymer Science vol. 76, Issue 13, p. 1870-1875; 2000.*

(Continued)

*Primary Examiner*—Long V Le
*Assistant Examiner*—Saurel J Selkin
(74) *Attorney, Agent, or Firm*—Blakely Sokoloff Taylor & Zafman LLP

(57) ABSTRACT

An echogenic catheter, such as a needle catheter, formed at least in part of an intrinsically conductive organic polymer for providing a highly conductive surface in combination with an improved ability to ultrasonically image the catheter, and a method of performing a medical procedure using a catheter of the invention.

20 Claims, 2 Drawing Sheets

U.S. PATENT DOCUMENTS

| | | | |
|---|---|---|---|
| 5,782,239 A * | 7/1998 | Webster, Jr. | 600/374 |
| 5,843,076 A * | 12/1998 | Webster et al. | 606/41 |
| 5,928,155 A * | 7/1999 | Eggers et al. | 600/526 |
| 6,004,269 A * | 12/1999 | Crowley et al. | 600/439 |
| 6,007,488 A | 12/1999 | Jaker et al. | |
| 6,099,745 A * | 8/2000 | McKenney et al. | 216/13 |
| 6,123,718 A * | 9/2000 | Tu et al. | 607/113 |
| 6,246,898 B1 | 6/2001 | Vesely et al. | |
| 6,283,947 B1 | 9/2001 | Mirzaee | |
| 6,371,915 B1 | 4/2002 | Koger et al. | |
| 6,375,615 B1 * | 4/2002 | Flaherty et al. | 600/439 |
| 6,414,086 B1 | 7/2002 | Wang et al. | |
| 6,457,350 B1 | 10/2002 | Mitchell | |
| 6,490,483 B2 | 12/2002 | Willis | |
| 6,528,199 B1 | 3/2003 | Mercuri et al. | |
| 6,554,801 B1 | 4/2003 | Steward et al. | |
| 6,592,580 B1 | 7/2003 | Stockert | |
| 6,610,005 B1 | 8/2003 | Tao | |
| 6,622,731 B2 * | 9/2003 | Daniel et al. | 128/898 |
| 6,641,540 B2 | 11/2003 | Fleischman et al. | |
| 6,661,875 B2 | 12/2003 | Greenwald et al. | |
| 6,685,657 B2 | 2/2004 | Jones | |
| 6,692,466 B1 | 2/2004 | Chow et al. | |
| 6,706,053 B1 | 3/2004 | Boylan et al. | |
| 6,716,166 B2 * | 4/2004 | Govari | 600/437 |
| 6,718,628 B2 | 4/2004 | Munshi | |
| 6,752,767 B2 * | 6/2004 | Turovskiy et al. | 600/564 |
| 6,765,144 B1 | 7/2004 | Wang et al. | |
| 6,841,213 B2 | 1/2005 | Parsonage et al. | |
| 6,855,124 B1 | 2/2005 | Gonzalez et al. | |
| 6,999,821 B2 | 2/2006 | Jenney et al. | |
| 7,037,271 B2 * | 5/2006 | Crowley | 600/463 |
| 7,220,233 B2 * | 5/2007 | Nita et al. | 601/2 |
| 7,285,108 B2 | 10/2007 | Koerner et al. | |
| 2003/0014100 A1 | 1/2003 | Meens et al. | |
| 2003/0018293 A1 | 1/2003 | Tanghoj et al. | |
| 2003/0093107 A1 | 5/2003 | Parsonage et al. | |
| 2003/0109823 A1 | 6/2003 | Hobot et al. | |
| 2003/0167056 A1 | 9/2003 | Jahns et al. | |
| 2003/0181928 A1 | 9/2003 | Vidlund et al. | |
| 2004/0024371 A1 | 2/2004 | Plicchi et al. | |
| 2004/0044286 A1 * | 3/2004 | Hossack et al. | 600/462 |
| 2004/0059328 A1 | 3/2004 | Daniel et al. | |
| 2004/0068191 A1 | 4/2004 | Seward et al. | |
| 2004/0077976 A1 | 4/2004 | Wilson | |
| 2004/0111141 A1 | 6/2004 | Brabec et al. | |
| 2004/0143160 A1 | 7/2004 | Couvillon, Jr. | |
| 2004/0267156 A1 | 12/2004 | Turovskiy et al. | |
| 2005/0070844 A1 | 3/2005 | Chow et al. | |
| 2005/0234289 A1 | 10/2005 | Anstadt et al. | |
| 2005/0261670 A1 | 11/2005 | Weber et al. | |

FOREIGN PATENT DOCUMENTS

| | | |
|---|---|---|
| EP | 1430848 A1 | 6/2004 |
| WO | WO-9719645 | 6/1997 |
| WO | WO-9911182 | 3/1999 |

OTHER PUBLICATIONS

In vitro evaluation of phosphonylated low-density polyethylene for vascular applications; Caldwell et al.; Journal of Biomedical Materials Research; vol. 62, Issue 4, p. 514-524; 2002.*

Stenger-Smith, Intrinsically electrically conducting polymers. Synthesis, characterization, and their applications, 1998, Prog. Polym. Sci., vol. 23, 57-79.*

PCT Search Report for PCT International Application No. US2007/009588, mailed Nov. 28, 2007 (13 pages).

Abbott Cardiovascular Systems In, *International Preliminary Report on Patentability* dated Jun. 12, 2008, PCT/US2006/044628.

Kimura, B J., et al., "Distortion of intravascular ultrasound images because of nonuniform angular velocity of mechanical-type transducers", *American Heart Journal*, vol. 132, No. 1, Part 1, (1996), 328-336.

Abbott Cardiovascvular Systems In, *International Preliminary Report on Patentability* mailed Nov. 27, 2008 in PCT Application No. PCT/US2007/009588.

Abbott Cardiovascvular Systems In, *International Preliminary Report and Written Opinion* dated May 18, 2007, PCT/US2006/044628.

* cited by examiner

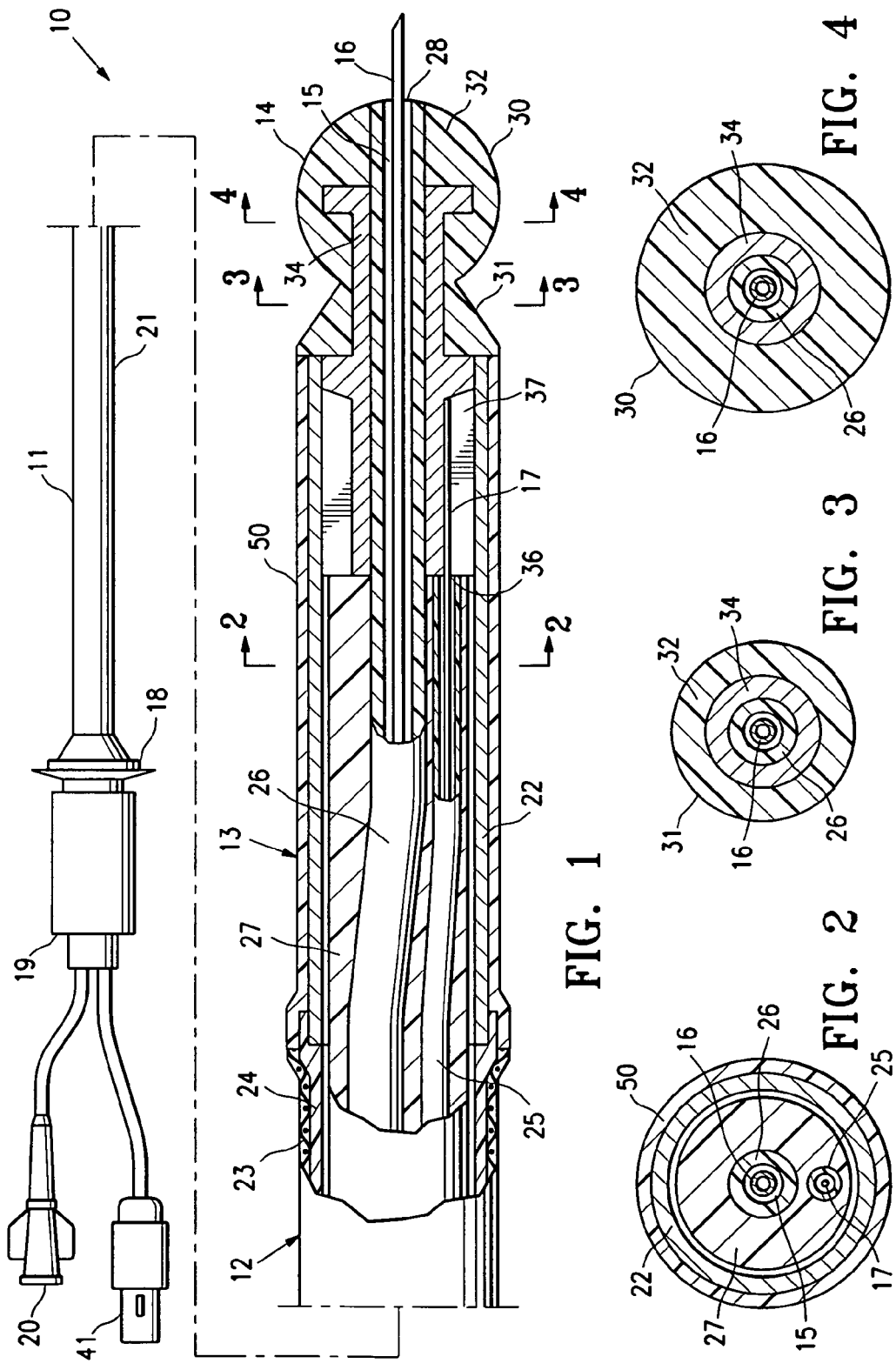

ECHOGENIC NEEDLE CATHETER CONFIGURED TO PRODUCE AN IMPROVED ULTRASOUND IMAGE

BACKGROUND OF THE INVENTION

The invention relates to the field of medical devices, and more particularly to echogenic catheters, such as needle catheters.

An essential step in treating or diagnosing cardiac tissue or cardiovascular diseases using an interventional catheter is the proper placement of the catheter at a desired location within the patient, which consequently requires accurate imaging of the catheter location within the patient. Although various methods of imaging catheters within a patient are possible, ultrasonic imaging (also referred to as acoustic imaging) would provide several advantages. For example, ultrasonic imaging is very safe for the expected extended time periods required for therapy guidance, unlike CT/EBCT (Electron Beam Computed Tomography) or bi-planar fluoroscopy. Additionally, ultrasound is relatively inexpensive compared to other imaging modalities such as MRI or CT/EBCT, and can provide tissue diagnostics such as wall motion and thickness information.

However, one difficulty is visualization anomalies, including artifacts and overly bright images, in the ultrasonic images of catheters. Such artifacts can provide a misleading and inaccurate impression of the shape and/or location of the catheter within the patient. Additionally, catheter elements can appear so bright and large on the ultrasonic image (called "blooming") due to their highly reflective nature relative to the anatomy, especially at the gain settings typically used to image the anatomy, that the image of the adjacent anatomy is obscured by the catheter image. For example, metallic portions of catheters can produce strong/high amplitude echoes (bright images), with a pyramid artifact (i.e., a pyramid shape of reverberation ("ringing") images trailing off in the viewing direction). Similarly, most thermoplastic catheter shafts produce strong/high amplitude direct echoes (bright images). If the gain settings of the ultrasonic imaging system are reduced to improve the image of the catheter (reduce its image and artifact brightness), the image of the anatomy fades significantly to the point of being less visible or not visible at all. Therefore, it would be a significant advance to provide a catheter with improved imaging characteristics by two-dimensional and three-dimensional ultrasonic imaging systems for enhancing the diagnosis and guidance of treatments in the body.

SUMMARY OF THE INVENTION

The invention is directed to an echogenic catheter, such as a needle catheter, configured to result in an improved ultrasonic image of the catheter, and a method of performing a medical procedure using a catheter of the invention. A catheter of the invention is formed at least in part of an intrinsically conductive organic polymer, for providing a highly conductive surface in combination with an improved ability to ultrasonically image the catheter. One aspect of the invention is directed to a method of performing a medical procedure using a catheter of the invention having a distal tip electrode formed of the intrinsically conductive polymer, in which the catheter distal tip is advanced into contact with a patient's heart wall under ultrasonic imaging, to perform a procedure such as generating an electrocardiogram. The catheter is typically a needle catheter, such that the distal tip of the catheter must be positioned accurately for delivery of an agent into the patient's heart wall from the catheter needle.

In a presently preferred embodiment, the echogenic catheter is configured for percutaneous transluminal advancement into a chamber of the patient's heart, although a variety of alternative catheter configurations may be used. An echogenic catheter of the invention generally comprises an elongated shaft having a proximal shaft section, a distal shaft section, a lumen extending therein from a proximal to a distal end of the shaft, and a polymeric distal tip at the distal end of the elongated shaft, which is formed at least in part of an intrinsically conductive organic polymer, and which is electrically connected to a conductor such that the distal tip is an electrode. The polymeric conductive distal tip typically has a distal portion of the shaft lumen in communication with a proximal portion of the shaft lumen and with a port at a distal end of the distal tip. In the embodiment in which the catheter is a needle catheter, a needle is slidably disposed in the shaft lumen, such that the needle has a distal end which extends distally from the distal tip port in an extended configuration. However, the catheter lumen can be configured for a variety of suitable uses.

The distal tip of the catheter is formed of a non-metallic conductive polymer in order to function as an electrode. Intrinsically (or inherently) conductive polymers (ICPs) are organic polymers which are electrically conductive without requiring the quantities of metal or carbon conductive additives commonly doped into nonconductive polymers to render them conductive. Common conductive additives include carbon blacks, metal (e.g., tungsten) powder, and metal or carbon fibers. Conventional poorly conductive and nonconductive polymers typically require relatively sizable percentages of these additives in order to form conductive tips. As a result, because metals and carbon are not polymers, they can disadvantageously affect the performance characteristics, such as the strength, flexibility and softness, of the distal tip. Additionally, metal additives can impair the ability to ultrasonically image the distal tip as discussed in more detail below. In contrast, the ICPs are sufficiently conductive without requiring the ultrasound image-impairing metal or carbon conductive additives.

A variety of suitable ICPs can be used including polyacetylene, polypyrrole, polythiophene, polyaniline, and polyparaphenylene vinylenes. Presently preferred ICPs include the highly biocompatible polypyrroles and polyanilines. For example, in one embodiment, the ICP is ST-Poly, which is a polypyrrole commercially available from Central Corporation of Japan. In another embodiment, the ICP is a polyaniline such as EEONOMER® that is commercially available from Eeonyx Corporation, or Panipol master batches available from Panipol Ltd of Finland. EEONOMER® loaded heterogeneous plastic alloys (e.g., thermoplastic polyolefin) exhibit at least a 10 fold increase in conductivity compared to high structure carbon black loaded alloys at the same loading level.

In a presently preferred embodiment, the distal tip is formed of a blend of the ICP with a low-conductive polymer matrix material. The terminology "low-conductive polymer" should be understood to refer to polymers which are non-conductive or so poorly conductive that the polymer will not function as an electrode absent a conductive additive. The low-conductive matrix polymer(s) of the blend preferably provides desired distal tip performance characteristics such as strength, flexibility, lubricity and the like, and the ICP of the blend provides the required degree of conductivity in accordance with the invention. A variety of suitable low-conductive matrix polymers, commonly used to form flexible distal tips of transluminal catheters, can be used including polyurethanes, polyolefins, and the like.

The ICPs readily blend or otherwise combine with the matrix polymer materials, and preferably possess relatively high thermal oxidative stability (e.g., up to about 300° C.) which facilitates processing the ICPs into the matrix polymer material without degradation or loss of conductivity. Consequently, the ICPs can be melt-processed with a variety of commonly used low-conductive matrix polymers, for ease of manufacturability and without the compounding difficulties of metal or carbon additives. Compared to conductive metal-filled systems, the ICPs provide substantial weight savings, flexibility, durability, low-temperature processibility, and tailored reproducible conductivity. Additionally, due to the improved compatibility with the matrix polymer, the ICPs preferably have reduced sloughing compared to carbon loaded formulations, and preferably do not disadvantageously affect the cohesive strength of the matrix polymer.

The ICP distal tip electrode facilitates ultrasonic imaging of the catheter distal end within the patient, compared to a conventional metallic tip electrode, by reducing the amount of metal in the distal tip. Specifically, metallic material in a conventional catheter distal tip absorbs stores and then reemits the sonic energy of the ultrasonic imaging device, causing the metal in the tip to ring like a bell, sending out ultrasonic energy until the sonic energy that it has stored is depleted. This absorbed, stored and then reemitted sonic energy is received by the ultrasonic imaging device and creates images behind the catheter tip that decrease in brightness and size as the stored sonic energy is depleted, forming the tip pyramid artifact. On the other hand, polymeric materials produce echoes from their surfaces in the body that are usually of less amplitude than the thick metallic surfaces of conventional electrode tips. Additionally, polymeric materials are generally more dissipative of sonic energy than metallic materials and thus, if any pyramid artifact is produced, it is of smaller amplitude than those produced by tips/electrodes formed completely of metal or of a higher proportion of metallic materials. A disadvantageously bright/long duration/large tip pyramid artifact obscures the actual image of the catheter tip and surrounding anatomy. In contrast, a distal tip of the invention, configured to minimize the amount of metallic material at the distal tip, reduces the amount of sonic energy that the tip stores and then reemits to thereby reduce the brightness and duration of the tip pyramid artifact. The soft polymeric distal tip completely eliminates, or at least reduces, the tip pyramid artifact of prior metallic or metallic/polymer hybrid electrode catheter tips.

In one embodiment, metallic material is present in the distal tip, for example in the form of radiopaque (e.g., tungsten) powder compounded with or otherwise added to the distal tip polymeric material, or in the form of a metallic tubular member extending within the distal tip. Although the amount of metallic material present may be sufficient to produce a tip pyramid artifact, the resulting tip pyramid artifact is of a desired minimized brightness and duration. Specifically, in some embodiments, the presence of the pyramid artifact at a reduced level relative to conventional fully metallic distal tip electrodes is desirable to more reliably differentiate the image of the catheter tip from the image of the catheter body and thus indicate that the tip of the catheter is being imaged, but in a manner that doesn't substantially obscure the image of the adjacent anatomy.

As discussed above, the polymeric distal tip of the invention prevents or reduces the tip pyramid artifact image. However, in the absence of a direct echo from the tip, the only ultrasonic image of the tip may be that due to the absorbed, stored and then reemitted sonic energy (i.e., the tip pyramid artifact). As a result, in a presently preferred embodiment, the polymeric distal tip has a spherical shape, as set forth in copending, commonly assigned U.S. patent application Ser. No. 11/293,420 ('420 Application"), incorporated by reference herein in its entirety. The spherical distal tip shape is configured to produce direct echoes, from a large angular range, and thereby prevents or minimizes the potential for misreading the position of the distal tip from the ultrasonic image, by avoiding the absence of an imaged direct echo from the distal tip. As discussed in the '420 Application, the spherical distal tip shape produces diffuse echoes such that the distal tip is directly imaged over a range of angles (relative to the catheter) substantially greater than 180°. Thus, the conductive polymeric distal tip of the invention, provided with a spherical shape, facilitates accurately positioning the catheter distal tip under ultrasonic imaging by providing an imaged direct echo with little or no tip pyramid artifact over a wide range of angles (i.e., with the catheter tip oriented in the patient at a wide variety of angles relative to the ultrasonic imaging device outside of the patient). The imaged direct echo indicates the actual location of the distal tip in the patient, unlike a tip pyramid artifact (if present) which is located behind the actual location of the catheter tip due to the delay in reemitting the sonic energy in the direction of the imaging device.

A variety of suitable methods can be used to form an ICP distal tip of the invention. In one embodiment, the ICP-matrix polymer blend is injection molded to form the distal tip. In an alternative embodiment, an ICP outer layer is added to the surface of a low-conductive polymer distal tip, using a variety of suitable methods such as spraying, dipping, plasma deposition under vacuum, printing, or brush painting, and most preferably by spray or dip coating. In one embodiment, the surface of the low-conductive polymer (e.g., a polyurethane) is modified with a functionalizing surface treatment before the ICP is applied. For example, a phosphonylation or sulfonation surface activation treatment, followed by polymerizing an ICP such as polypyrrole or polyaniline on the functionalized surface of the low-conductive polymer, results in a layer ICP bonded to the functionalized surface of the underlying low-conductive polymer with superior cohesion and adhesion. Optionally, a method of the invention includes binding one or more additional layers or lamellae of conductive polymer thereon, which facilitates tailoring the electrical conductivity of the tip electrode with negligible impact on the structural (low-conductive) polymer's mechanical properties such as abrasive resistance. Typically, the conductive polymer is self-activated such that an additional surface treatment or adhesive layer is not required in order to bind another layer of the same or a different ICP (i.e., by its very nature it is in a state which forms strong bonds to subsequently applied layers of ICP). For example, doping emeraldine base with acid (dopant) results to a conductive emeraldine salt of polyaniline, which provides a conductive, self-activated surface, ready for optionally adding one or more additional sublayers of ICP.

One aspect of the invention is directed to a method of performing a medical procedure using a polymeric distal tipped echogenic catheter of the invention. The distal tip functions as an electrode primarily for diagnostic purposes, but, alternatively, for therapeutic purposes (e.g., defibrillation or ablation) in which energy is delivered via the polymeric conductive distal tip of the catheter if desired.

In one embodiment, a method of the invention generally comprises advancing within a patient's anatomy an echogenic needle catheter comprising an elongated shaft, a polymeric distal tip which is formed at least in part of an ICP and which has a port at a distal end of the distal tip, and preferably a needle which extends distally from the distal tip port in an extended configuration. The method includes directing sonic energy at the distal tip from an ultrasonic imaging device, to produce an ultrasonic image of the distal tip with eliminated or reduced pyramid artifact compared to a distal tip having a metallic tip electrode, and positioning the distal tip at a desired location within the patient.

A catheter distal tip of the invention minimizes the amount of metal in the tip and thus reduces its echo amplitudes, and reduces or eliminates its pyramid artifact. The ICP conductive materials have improved electrical, mechanical and melt-flow properties. Specifically, a catheter distal tip of the invention formed of the ICP has an improved combination of good cohesive strength, flexibility, and high conductivity, unlike prior "conductive polymeric" distal tips which required high levels of metallic or carbon doping to be conductive. Additionally, the ICP conductive blends have greatly reduced compounding difficulties compared with the prior metal- or carbon-doped formulations. These and other advantages of the invention will become more apparent from the following detailed description and exemplary drawings.

BRIEF DESCRIPTION OF THE DRAWINGS

FIG. 1 is an elevational view, partially in section, of an echogenic needle catheter embodying features of the invention, having a polymeric conductive distal tip.

FIGS. 2-4 are transverse cross sectional views of the catheter of FIG. 1, taken along lines 2-2, 3-3, and 4-4, respectively.

DETAILED DESCRIPTION OF THE INVENTION

Figure 5:
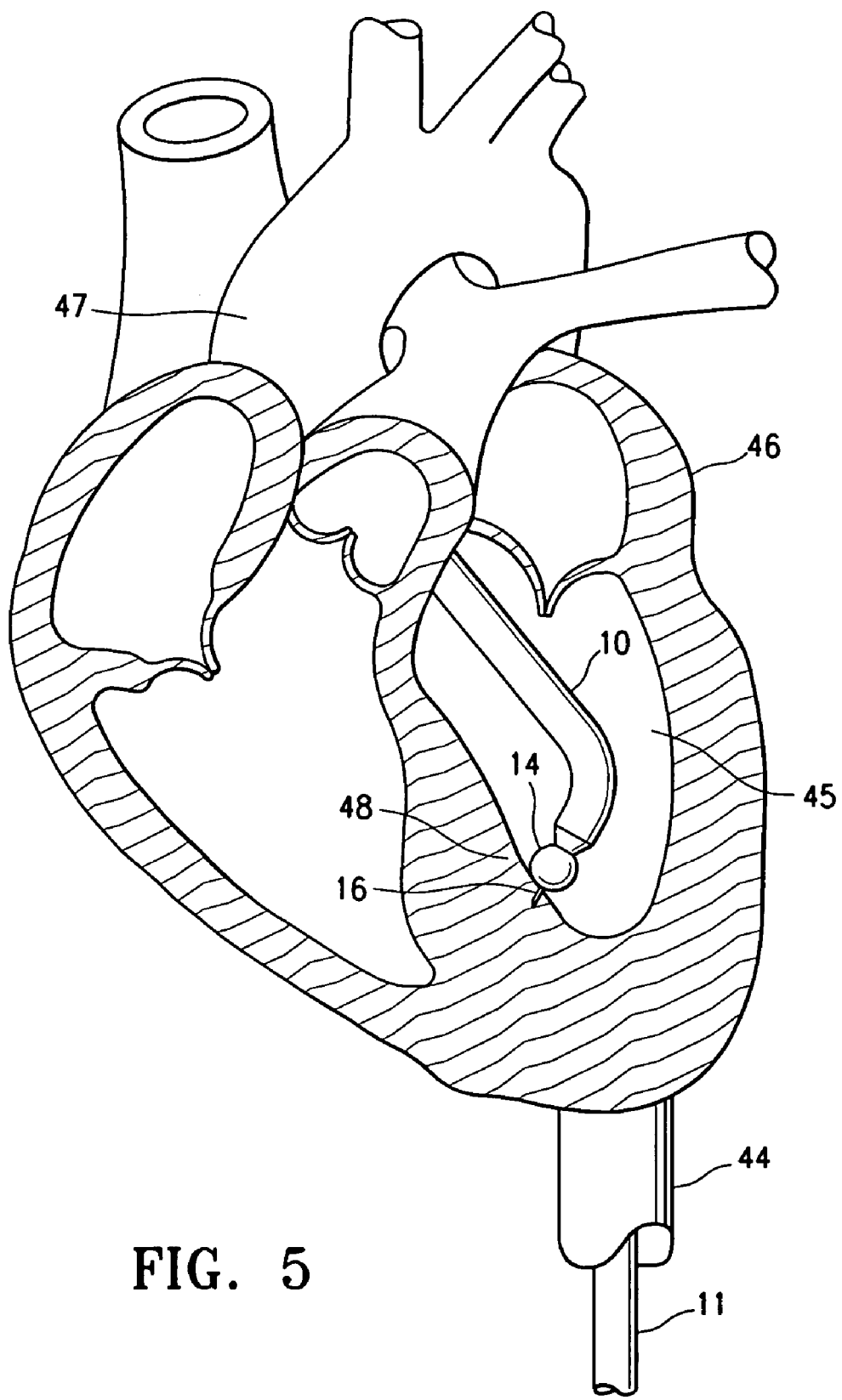
FIG. 5 illustrates the catheter of FIG. 1 within a left ventricle of a patient's heart.

FIG. 1 illustrates a needle catheter 10 which embodies features of the invention. In the embodiment illustrated in FIG. 1, the needle catheter 10 generally comprises an elongated shaft 11 having a proximal shaft section 12, a distal shaft section 13, and a needle containing lumen 15, and a distal tip 14 at the distal end of the shaft 11. A needle 16 is slidably disposed within the lumen 15 of the shaft, with an extended configuration in which the needle distal end extends distally from the distal end of the catheter (see FIG. 1), and with a retracted configuration (not shown) in which the needle distal end is proximally retracted into the catheter lumen 15. In the illustrated embodiment, the catheter 10 has an elongated deflection member 17 (e.g., a tendon wire) connected to a deflection control mechanism 18 at a proximal adapter 19, for deflecting the distal end of the catheter 10. To effectively deflect the distal end of the catheter the deflection member 17 is preferably near the surface of the shaft in the deflecting (curving) portion. However, the catheter 10 can have a variety of suitable catheter configurations including a non-deflecting configuration. The proximal adapter 19 on the proximal end of the shaft 11 has a port 20 configured for providing access to the needle 16 for delivery of an agent, or for aspiration, through the lumen of the needle 16. A variety of operative connectors may be provided at the proximal adapter 19 depending on the desired use of the catheter 10. FIGS. 2-4 illustrate transverse cross sectional views of the catheter 10 of FIG. 1, taken along lines 2-2, 3-3, and 4-4, respectively.

In the embodiment of FIG. 1, the shaft 11 comprises an outer tubular body member 21, and an inner tubular member 26 which extends within the outer tubular body member 21 and which defines the needle containing lumen 15 of the shaft 11. The inner tubular member 26 is formed of a single layered, integral one-piece tube extending from the proximal to the distal end of the catheter, or alternatively of multiple sections of tubing with communicating lumens, and/or a multilayered tube(s). The distal tip 14 has a lumen extending through the distal tip, which forms a distal section of the needle containing lumen 15 and which is in communication with a port 28 at a distal end of the distal tip 14. In the embodiment illustrated in FIG. 1, a distal section of the inner tubular member 26 defines the section of the needle containing lumen 15 within the distal tip 14. However, a variety of suitable configurations may be used including an embodiment in which the distal end of the inner tubular member 26 is proximal to the distal end of the catheter 10.

The distal tip 14 functions as an electrode, and thus has a conductor (e.g., a metal wire) electrically connected thereto. In the embodiment illustrated in FIG. 1, the deflection member 17 is electrically connected to the distal tip 14 (via member 34 discussed in more detail below), such that the member 17 doubles as a deflection and a conduction wire. However, a variety of suitable configurations can be used including embodiments in which a separate conduction wire is provided which extends the entire length of the catheter or which extends between the deflection member 17 and the distal tip 14. Therefore, it should be understood that in alternative embodiments, the shaft 11 may include a separate conductor lumen extending therein. The conduction wire is soldered, welded, mechanically crimped or imbedded or otherwise connected to electrical connect to the distal tip 14. At the proximal end, the conduction wire 17 is electrically connected to an electrical connector 41 at the proximal adapter 19, for connecting the catheter 10 to diagnostic or therapeutic equipment (not shown).

In the embodiment of FIG. 1, a high strength support member 34, such as a short length of a metal (e.g., stainless steel) hypotube, secures the distal tip 14 to the distal end of the outer tubular member 21 of the catheter shaft 11. The support member 34 has a flared distal end at/near the center of the distal tip 14 to securely attach thereto. The catheter tip 14 is configured for mechanically strong, secure attachment and support, while nonetheless minimizing the amount of metal at the catheter distal end in order to minimize the brightness and duration of the tip pyramid artifact in the ultrasonic image of the catheter distal end.

In accordance with the invention, distal tip 14 is formed at least in part of an intrinsically conductive polymer (ICP). In one embodiment, the distal tip ICP is selected from the group consisting of polyacetylene, polypyrrole, polythiophene, polyaniline, and polypara-phenylene vinylenes. In a presently preferred embodiment, the ICP is a polypyrrole or a polyaniline.

In a presently preferred embodiment, the polymeric conductive distal tip 14 has a wall 32 molded or otherwise formed from a polymeric blend of the ICP and a matrix polymer. The resulting distal tip wall 32 is preferably a uniform blend of the ICP/matrix polymer (i.e., the ICP is uniformly distributed throughout the distal tip wall). The ICP and matrix polymer are typically compounded together and injection molded, although the term "blend" should be understood to refer to a variety of suitable combining methods. The matrix polymer is typically a low-conductive polymer (i.e., non-conductive or poorly conductive), such as a polyurethane (e.g., PELLETHANE), polyethylene, polypropylene, styrene isobutyl styrene (SIBS), or polyvinylidiene hexafluoropropylene elastomer (PVDF-HFP). The low-conductive polymers generally have a conductivity of less than about 0.0005 S/m.

The blend comprises a sufficient amount of ICP material so that the distal tip 14 functions as an electrode when electrically connected to diagnostic or therapeutic equipment. The amount of ICP is typically a relatively large percent by volume of the distal tip, to maximize the conductivity of the distal tip. In one embodiment, the ICP is about 1% to about 30% by weight of the blend, depending on the desired conductivity of the distal tip 14. Preferably, the amount of ICP provides sufficient conductivity, without disadvantageously affecting manufacturability or performance characteristics of the distal tip 14 (e.g., the ability to compound and melt-form the blend, or the distal tip strength, flexibility and abrasion resistance, etc.). The conductivity of the resulting distal tip blend is about 0.01 to about 100 Siemens per meter (S/m), and more preferably about 0.1 to about 10 S/m. The blend has a resistance of about 1000 ohms. The use of the blend facilitates tailoring the amount of ICP in order to provide a specific desired conductivity together with manufacturability and performance characteristics. For example, minimizing the amount of ICP is advantageous for minimizing cost.

In the illustrated embodiment, the polymeric conductive distal tip 14 is a separate member bonded to the distal end of the outer tubular body member 21. However, in an alternative embodiment, the polymeric conductive distal tip 14 can be formed integrally with at least a section of the shaft 11 proximal thereto. The ICP-matrix polymer blend is typically injection molded around the support member 34 to form the distal tip 14 of the embodiment of FIG. 1, and a proximal end section of the resulting distal tip 14 is bonded, for example using an adhesive, to the distal end of the outer member 21.

In one embodiment, the polymeric conductive distal tip 14 includes a radiopaque material, such that the distal tip 14 is radiopaque. Preferably, the radiopaque material is distributed within the blend. For example, tungsten powder compounded or otherwise mixed into the blend before the distal tip 14 is molded, in an amount of about 20 to about 60% by weight of the blend, renders the distal tip 14 radiopaque. Such quantities of radiopaque material do not produce a distal tip with a sufficiently high conductivity to function as an electrode as required by the invention. Similarly, in the absence of the radiopaque additive, the amount of the metallic material in the distal tip 14 is minimized to an extent that the tip 14 would not be visible under fluoroscopy within the patient's vasculature during a typical procedure.

In an alternative embodiment, the polymeric conductive distal tip 14 has a wall formed of a low-conductive polymer (i.e., not blended with the ICP) and an outer layer formed at least in part of an ICP bonded to the low-conductive polymer wall. The conductive ICP outer layer is typically significantly thinner than the underlying low-conductive polymer wall of the catheter distal tip, and the underlying low-conductive polymer wall is otherwise similar to the wall 32 of the embodiment of FIG. 1. The underlying low-conductive polymer wall consists essentially of the low-conductive polymer, with the ICP outer layer thereon, although it may have a radiopaque or lubricious additive, or an inner (e.g., lubricious) layer as is conventionally known for catheter distal tips.

In one embodiment, the low-conductive polymer distal tip is treated with a functionalizing surface treatment to produce a functionalized distal tip 14 surface which is subsequently coated with the ICP, resulting in molecularly bound ICP. Specifically, a low-conductive (e.g., polyurethane) distal tip wall is functionalized using a phosphonylation or sulfonation surface treatment to provide a more bondable outer layer for attachment of ICPs such as polyaniline. For example, a functionalized polymer with phosphonyl surface or a sulfonyl surface has surface-modifying end groups which function as surface active oligomers covalently bonded to the base polymers such as polyurethane, pure styrene-butadiene-styrene triblock copolymer (Vector), or styrene-ethylene/butylene-styrene triblock elastomer forming the underlying wall of the echogenic polymer tip. These active end groups will not compromise the bulk properties but can promote the bonding of an ICP to be coated onto the base echogenic polymer tip. In addition, the sulfonation will improve the ion transport and conductivity of a base styrene-ethylene/butylene-styrene triblock elastomer.

The ICP is formed and remains securely bound to the underlying low-conductive polymer through an in-situ polymerization method. Optionally, additional sublayers of ICP are applied to the resulting self-activated ICP using the same in-situ polymerization method, typically to produce a final outer conductive ICP layer made up of a total of up to about 3 sublayers of ICP. The resulting outer conductive ICP layer is highly conductive despite being relatively thin, and is echo compatible.

To provide the ICP outer layer, a solution of the ICP can be applied to the surface of a low-conductive polymer by conventional coating techniques. For example, the ICP commercially available as BAYTRON (poly(3,4-ethylenedioxythiophene) (PEDT)), and more specifically, a mixture of BAYTRON® P, which is a waterborne dispersion of the polymer complex poly(3,4-ethylenedioxy-thiophene)/polystyrene sulfonate (PEDT/PSS), can be coated onto the surface of the distal tip, and polymerized thereon, to produce an outer conductive ICP layer having a wet film thickness of about 6 micrometers, and a resistivity (specific electrical resistance) of less than about $10^4$ ohm meter. The mixture contains 42.9% by weight BAYTRON® P, 2.6% by weight N-Methyl-2-pyrrolidinone, 0.9% by weight Silquest® A 187 (a polyepoxysilane adhesive additive), 53.3% by weight isopropanol, and 0.3% by weight Dynol 604, and results in about 2.6 g of BAYTRON® P applied per square meter.

A wide variety of commonly used low-conductive polymers can be thus modified, to form a multifunctional material capable of carrying or dissipating significant electrical charge. The resulting conductivity of the ICP-coated, functionalized distal tip is typically tailored over a range of about 0.1 S/m to about 10 S/m by having more/fewer layers of ICP, without significantly affecting the performance characteristics provided by the underlying low-conductive polymer.

In one embodiment, the outer conductive layer is a blend of an ICP and a matrix polymer (similar to the blend discussed above in relation to the embodiment of FIG. 1), applied to the underlying low-conductive polymer wall of the distal tip, for example by dip or spray coating.

In the illustrated embodiment, the polymeric conductive distal tip 14 has a spherical shape. Specifically, distal tip 14 has a distal spherical portion 30, and a proximal support portion 31 which has a proximal end connected to the distal end of a distal portion of outer tubular body member 21. The spherical portion 30 has a curving outer surface extending around the circumference of the distal tip to an included angle substantially greater than 180°, as discussed in the '420 application previously incorporated by reference herein. The proximal support portion 31 has a conically shaped section with an outer surface tapering distally to a smaller outer diameter. The support portion 31 is formed of a sufficiently strong material(s) to securely connect and support the spherical distal tip 14 during use of the catheter 10, and is typically formed of the same material as the spherical portion of the tip 14. The length and tapering angle of support portion 31 is preferably chosen such that it will not shield or block the spherical distal tip portion 30 from sonic energy over the designed range of distal tip imaging angles.

Although not illustrated, at least a second electrode is typically provided on the shaft 11, with a corresponding electrical conductor. The second electrode, functions, for example, as a reference electrode for the electrode that is the polymeric conductive distal tip 14. The second (e.g., reference) electrode is preferably provided on the proximal shaft section 12 such that it is located out of the patient's heart chamber, preferably superior to the heart chamber, such as in the aortic arch or a vena cava, for tip tissue contact/tissue ECG monitoring applications and/or about one centimeter behind the tip for ECG anomaly detection applications. In applications where pacing is anticipated to be required, many electrodes may be spaced along the distal portion of the catheter shaft, such that, at least, one electrode (with a surface electrode) or electrode pair will pace successfully at the current catheter position.

FIG. 5 illustrates the needle catheter 10 with the distal end of the catheter within the left ventricle 45 of the patient's heart 46. The catheter 10 is typically advanced in a retrograde fashion within the aorta 47, via the lumen of an introducer sheath which is inserted into the femoral artery. The catheter 10 illustrated in the embodiment of FIG. 1 is not configured for advancement over a guidewire, although in alternative embodiments and delivery sites, such as into veins or arteries, a guidewire lumen is provided in the shaft 11 for slidably receiving a guidewire therein. Additionally, in such vessel applications, the guidewire and catheter may be inserted into position using a guiding catheter that is first inserted into the introducer. In this intracardiac application, a deflecting mechanism is desired. By activating the deflection member 17 using the deflection control mechanism 18, the distal end of the catheter is caused to deflect away from the longitudinal axis of the shaft 11. With the distal end of the polymeric conductive distal tip 14 thus positioned in contact with a desired site of the ventricle wall, electrical data can be collected from the polymeric conductive distal tip 14. The electrical data (e.g., tissue contact ECG) facilitates tissue diagnostics (in combination with echo image ventricle wall motion measures) to determine if the site should be treated or not. The site can be treated by direct injection of a therapeutic agent, such as a biological or chemical agent, from the needle 16. FIG. 5 illustrates the distal end of the polymeric conductive distal tip 14 and the port 28 against the ventricle wall, with the needle 16 in the extended configuration advanced out the port 28 and into the cardiac tissue 48 of the ventricle wall. Multiple sites within the left ventricle can be thus accessed and treated using the catheter of the invention.

Although illustrated in the ventricle, a catheter 10 of the invention can be used to inject into the vessel wall or through the vessel into the myocardium or other adjacent tissues. Thus, although the distal needle port 28 is in the distal-most end of the polymeric conductive distal tip 14, coaxial with the longitudinal axis of the catheter shaft in the embodiment of FIG. 1, in alternative embodiments (not shown), the catheter has a needle port configured to direct the needle at an angle away from the longitudinal axis of the catheter (e.g., for injecting into or through a vessel). For example, the port through which the needle extends can be located eccentric to the longitudinal axis of the catheter or in a side wall of the catheter proximal to the distal end of the polymeric conductive distal tip 14, and the catheter configured for transvascular use.

Ultrasound can be used in conjunction with the catheter supplied ECG to provide tissue diagnostics by visualization of the wall motion and thickness. Additionally, the catheter 10 facilitates using ultrasonic imaging for visualization and positioning of the catheter 10. Specifically, with the catheter 10 distal end in the left ventricle (or other desired location within the cardiac anatomy), sonic energy is directed at the polymeric conductive distal tip 14 from an ultrasonic imaging device (not shown). The ultrasonic imaging device is typically an external device, a TTE probe (Transthoracic Echo, probe on the chest), although a TEE probe (Transesophageal Echo, probe in the throat), an ICE probe (Intracardiac Echo, probe in a cardiac chamber) or an IVUS (Intravascular Ultrasound, probe in a vessel) can alternatively be used.

The ultrasonic image of the distal tip has an eliminated or reduced pyramid artifact compared to a distal tip having a conventional metallic tip electrode. Specifically, the polymeric conductive distal tip 14 formed of an ICP uses less metal in the distal tip than a solid metal distal tip or band electrode or a metal/polymer conductive blend, and any metallic portions at the distal tip 14 are in contact with the sonic energy damping plastic material thereof, so that the tip pyramid artifact has a desired low level of brightness and shorter duration or is absent entirely from the display. Additionally, in the embodiment having a spherical shape, the spherical polymeric conductive distal tip 14 reflects the sonic energy more diffusely than a non-spherical tip, to provide an ultrasonic image of the distal end of the catheter from a wide range of angles relative to the viewing direction of the ultrasonic imaging device.

A variety of suitable catheter shaft designs can be used with the polymeric conductive distal tip 14 of the invention, including deflectable needle catheter shafts described in U.S. patent application Ser. No. 10/676,616 (filed Sep. 30, 2003), and U.S. Ser. No. 11/293,420 (filed Dec. 2, 2005), each of which is incorporated by reference herein in its entirety. For example, the proximal portion of outer tubular body member 21 of the shaft 11 is typically formed at least in part of metal, such as a polymer reinforced with a braided or coiled metallic filaments or a hypotube or slotted metallic tube, although it may alternatively or additionally consist of a high modulus polymer. In the illustrated embodiment, the shaft 11 has a braided body layer 23 extending distally from a proximal end section of the catheter, and comprising a polymeric material encapsulating a wound tubular support layer typically formed of braided filaments of a metal such as stainless steel. The braid is encapsulated by an outer layer which is typically formed of multiple sections of differing durometers/polymers joined end to end to provide a stiffness transitions along the length of the catheter. The braid is formed over a polymeric core layer 24. In the illustrated embodiment, the distal portion of the tubular body member 21 of the shaft 11 comprises a cage 22 typically formed of a slotted metallic tube. The compression cage 22 is configured to deflect laterally as discussed in the '616 application, incorporated by reference above. The cage 22 is typically covered with an outer jacket layer 50.

The deflection member 17 extends within a lumen of a second inner tubular member 25, and is secured to the shaft adjacent to the distal end of the distal portion of tubular body member 21. In the illustrated embodiment, a stabilizing tubular member 27, typically comprising a dual lumen extrusion, is positioned within at least a section of the cage 22 to stabilize the position of the inner tubular members 25, 26 therein. The stabilizing member 27 is formed of a single section or multiple longitudinally adjacent sections of the tubing, and has a proximal end typically located within the cage 22 or a short distance proximal thereto. In alternative embodiments, the stabilizing tubular member 27 is omitted.

In the embodiment illustrated in FIG. 1, the support member 34 has a proximal end 36 electrically connected to the deflection/conductor member 17. Specifically, the support member 34 has two grooves on opposite sides of the proximal section of the member 34, and the distal end of the deflection/conductor member 17 is within one of the grooves. The support member 34 thus provides electrical connection to the distal tip 14, either by being embedded in a wall of the distal tip 14 formed of the ICP-matrix blend, or by being in contact with/electrically connected to an outer conductive ICP layer of the distal tip 14.

While the present invention is described herein in terms of certain preferred embodiments, those skilled in the art will recognize that various modifications and improvements may be made to the invention without departing from the scope thereof. For example, while discussed primarily in terms of a needle catheter, it should be understood that a variety of catheters can be used which embody features of the invention including balloon catheters, guiding catheters, ablation catheters, device delivery catheters and catheters that accommodate or incorporate sensors (i.e. temperature, chemical, oxygen, etc.). For example, the needle can be eliminated and solution infused through the empty lumen of the catheter (e.g., to inject directly into the bloodstream just proximal of the area to be treated). Additionally, although discussed primarily in terms of a distal tip formed of the ICP, it should be understood that the ICP can be used to form a conductive element on other locations on the catheter, such as on the outer or inner catheter shaft or the balloon.

Thus, the echogenic catheter features being disclosed are applicable to all types of catheters/other devices that may be guided by ultrasound and/or must be present in the anatomy during ultrasonic imaging. Additionally, although the catheter features are useful for use with 2D or 3D ultrasonic imaging systems, it should be noted that for the purpose of catheter guidance, a 3D echo system is preferred to the "slice" image provided by a 2D echo system. A 3D echo system produces images that can either be a see-through representation of large 3D volume of the anatomy and catheter or a 3D surface image of the same. In a 3D image, anatomic reference points abound in the image and, with a properly echogenic catheter (as described in this application), all portions of the catheter in the image volume may be seen, and the direction of the catheter shaft relative to the anatomy is easily visualized as described herein.

Moreover, although individual features of one embodiment of the invention may be discussed herein or shown in the drawings of the one embodiment and not in other embodiments, it should be apparent that individual features of one embodiment may be combined with one or more features of another embodiment or features from a plurality of embodiments.

What is claimed is:

1. An echogenic catheter, comprising
   a) an elongated shaft having a proximal shaft section, a distal shaft section, and a lumen extending therein from a proximal to a distal end of the shaft; and
   b) a polymeric distal tip at the distal end of the elongated shaft, which is formed at least in part of an intrinsically conductive organic polymer having an outer surface with a circumference angle substantially greater than 180 degrees, and which has a distal portion of the shaft lumen extending therein in communication with a proximal portion of the shaft lumen and with a port at a distal end of the distal tip, and which is electrically connected to a conductor extending at least through the distal shaft section such that the distal tip is an electrode, wherein the intrinsically conductive organic polymer is not doped with additional materials to aid electrical conductivity, wherein the conductor comprises a wire electrically connecting the distal tip to a distal end of the shaft to conduct a signal from the distal tip to a signal receiving device for generating an electrocardiogram, wherein the polymeric distal tip is a solid material molded around and in continual contact along a cylindrical outer surface of a metal support of the distal shaft section, and in continual contact along outer surfaces of an end flair of the metal support.

2. The catheter of claim 1 wherein the intrinsically conductive polymer is selected from the group consisting of polyacetylene, polypyrrole, polythiophene, polyaniline, and poly-para-phenylene vinylenes.

3. The catheter of claim 1 wherein the tip is a blend of the intrinsically conductive polymer and a low-conductive polymer matrix.

4. The catheter of claim 3 wherein the tip has a wall which is formed of the blend and which has a curved outer surface defining a distal leading face of the catheter having the port therein.

5. The catheter of claim 3 wherein the distal tip includes a radiopaque material different from the intrinsically conductive polymer, such that the distal tip is radiopaque, and wherein the amount of radiopaque material does not interfere with imaging of a surrounding anatomy.

6. The catheter of claim 5 wherein the radiopaque material is distributed within the blend.

7. The catheter of claim 1 wherein the distal tip has a wall formed of a low-conductive polymer and an outer layer formed at least in part of the intrinsically conductive polymer bonded to the low-conductive polymer, the outer layer having an inner surface bonded to the low-conductive polymer wall.

8. The catheter of claim 7 wherein the low-conductive polymer has a functionalized outer surface bonded to the intrinsically conductive polymer outer layer, the functionalized outer surface being a phosphonyl or sulfonyl surface.

9. The catheter of claim 1 wherein the catheter is needle catheter including a needle in the lumen of the shaft, which extends distally from the distal tip port in an extended configuration, and which has a lumen.

10. The catheter of claim 9 wherein the shaft comprises an outer tubular body member, and an inner tubular member therein, wherein the inner tubular member extends distally from a proximal end of the shaft and within the polymeric distal tip, and defines the lumen of the shaft which has the needle therein such that the needle is slidably disposed in the inner tubular member of the shaft.

11. The catheter of claim 1 including a second electrode on a proximal shaft section.

12. The catheter of claim 1 wherein the intrinsically conductive polymer provides the distal tip electrode with a relatively high conductivity of at least about 0.01 S/m.

13. The catheter of claim 1, wherein the conductor comprises an elongated deflection member with a distal end secured to the shaft and a proximal end coupled to the wire, the member is configured for deflecting a distal section of the catheter shaft; and the wire is configured to double as a deflection wire and as a conduction wire.

14. An echogenic needle catheter, comprising:
   a) an elongated shaft having a proximal shaft section, a distal shaft section, a lumen extending therein from a proximal to a distal end of the shaft, and a polymeric distal tip at the distal end of the elongated shaft, wherein the polymeric distal tip is formed at least in part of an intrinsically conductive organic polymer having an outer surface with a circumference angle substantially greater than 180 degrees, has a curved outer surface, an inner surface with a distal portion of the shaft lumen therein in communication with a proximal portion of the shaft lumen and with a port at a distal end of the distal tip, and is electrically connected to a conductor extending at least through the distal shaft section such that the distal tip is an electrode, wherein the intrinsically conductive organic polymer is not doped with additional materials to aid electrical conductivity, wherein the conductor comprises a wire electrically connecting the distal tip to a distal end of the shaft to conduct a signal from the distal tip to a signal receiving device for generating an electrocardiogram, wherein the polymeric distal tip is a solid material molded around and in continual contact along a cylindrical outer surface of a metal support of the distal shaft section, and in continual contact along outer surfaces of an end flair of the metal support; and b) a needle slidably disposed in the shaft lumen, which extends from the distal tip port in an extended configuration.

15. The needle catheter of claim 14 wherein the distal tip has a wall which is formed of a uniform blend of the intrinsically conductive organic polymer and a low-conductive polymer.

16. The needle catheter of claim 15 including a radiopaque material distributed within the blend, such that the distal tip is radiopaque, and wherein the amount of radiopaque material does not interfere with imaging of the surrounding anatomy.

17. The needle catheter of claim 14 wherein the intrinsically conductive polymer is selected from the group consisting of polyacetylene, polypyrrole, polythiophene, polyaniline, and polypara-phenylene vinylenes.

18. A method of performing a medical procedure within a patient, comprising:

a) advancing within the patient's vasculature an echogenic catheter, comprising i) an elongated shaft having a proximal end, a distal end, and a lumen;

ii) a polymeric distal tip at the distal end of the elongated shaft, formed at least in part of an intrinsically conductive organic polymer having an outer surface with a circumference angle substantially greater than 180 degrees, which has an outer surface, an inner surface with a distal portion of the shaft lumen extending therein in communication with a proximal portion of the shaft lumen and with a port at a distal end of the distal tip, and which is electrically connected to a conductor extending at least through the distal shaft section such that the distal tip is an electrode, wherein the intrinsically conductive organic polymer is not doped with additional materials to aid electrical conductivity, wherein the polymeric distal tip is a solid material molded around and in continual contact along a cylindrical outer surface of a metal support of the distal shaft section, and in continual contact along outer surfaces of an end flair of the metal support;

b) imaging the distal tip within the patient by directing sonic energy at the catheter from an ultrasonic imaging system, to produce an ultrasonic image of the distal tip with eliminated or reduced tip pyramid artifact compared to a distal tip having a metallic tip electrode, and positioning the distal tip at a desired location within the patient; and c) positioning the intrinsically conductive organic polymer of the distal tip of the catheter into abutting contact with a wall surface of a heart chamber of the patient, such that the distal tip conducts an electrical signal from the heart wall to a signal receiving device electrically connected to the catheter conductor, to thereby generate an electrocardiogram.

19. The method of claim 18 wherein the intrinsically conductive polymer provides the distal tip with a conductivity of about 0.01 to about 100 S/m, and wherein the electrical signal is conducted directly from the heart wall to catheter conductor or ECG by the distal tip.

20. The method of claim 18 wherein the catheter is a needle catheter having a needle in the shaft lumen which extends distally from the distal tip port in an extended configuration, and wherein positioning the distal tip of the catheter into abutting contact with the heart chamber wall positions the distal tip port against the heart chamber wall so that the needle in the extended configuration penetrates the heart chamber wall, and including extending the needle through the port and into the heart chamber wall.

* * * * *